United States Patent [19]

Shors

[11] Patent Number: 4,969,896

[45] Date of Patent: Nov. 13, 1990

[54] VASCULAR GRAFT PROSTHESIS AND METHOD OF MAKING THE SAME

[75] Inventor: Edwin C. Shors, Rancho Palos Verdes, Calif.

[73] Assignee: Interpore International, Irvine, Calif.

[21] Appl. No.: 305,375

[22] Filed: Feb. 1, 1989

[51] Int. Cl.$^5$ ............................................. A61F 2/06
[52] U.S. Cl. ........................................... 623/1; 600/36
[58] Field of Search ........................ 623/1, 12; 600/36

[56] References Cited

U.S. PATENT DOCUMENTS

| | | | |
|---|---|---|---|
| 3,479,670 | 11/1969 | Medell . | |
| 4,546,500 | 10/1985 | Bell . | |
| 4,617,932 | 10/1986 | Kornberg | 623/1 |
| 4,731,073 | 3/1988 | Robinson | 623/1 |
| 4,798,606 | 1/1989 | Pinchuk | 623/1 |

Primary Examiner—Alan W. Cannon
Attorney, Agent, or Firm—Lyon and Lyon

[57] ABSTRACT

A prosthesis for replacing parts of arteries and other blood vessels preferably has an inner tube suitable for use as a vascular graft in combination with external longitudinal ribs and a surrounding wrap which provides radial and longitudinal strength and resistance to kinking. The ribs separate the wrap from the inner tube, providing spaces between the wrap and tube to allow the tube to expand and contact, thus promoting isocompliance of the prosthesis with natural blood vessels.

16 Claims, 2 Drawing Sheets

VASCULAR GRAFT PROSTHESIS AND METHOD OF MAKING THE SAME

BACKGROUND OF THE INVENTION

1. Field of the Invention.

The field of the invention is prosthetic devices and, in particular, prostheses for replacing segments of blood vessels of the body.

2. Description of the Related Art

Vascular prostheses (i.e., artificial blood vessels) are used to replace diseased arteries or to provide access to blood by connecting a patient's artery to a vein. Vascular graft prostheses must be porous and made of a biocompatible material. The luminal surface must be thromboresistant and heal with a neointima or a pseudointima. This neointima must remain thin and not proliferate, to prevent eventually occluding the prosthesis. This physiological healing also helps prevent infection and transient occlusions.

Vascular prostheses undergo cyclic loading in response to cardiogenic blood pressure changes. As a consequence, the prostheses must be able to withstand fatigue. In addition, prostheses are sometimes under tensile stress intraoperatively when they are pulled subcutaneously. Normally, the tensile stress is minimal after completing the anastomosis. Nevertheless, tensile forces are exerted during kinking, when a prostheses is placed around a joint. Kink resistance is a desirable feature when placing a prostheses intraoperatively, in order to assure a patent lumen.

Compliance is another desirable feature of a vascular prosthesis. Compliance is the ability to expand and contract like a natural artery in response to changing blood pressure. Matching compliance of the prostheses with the compliance of the natural artery at the anastomosis is one of the most important requirements for long-term success of a small diameter vascular graft prosthesis. Without compliance, turbulence develops at the suture lines, causing intimal hyperplasia. Vascular prostheses should be designed to be isocompliant with the attached artery.

Various approaches have been taken to providing vascular graft prostheses. Some prostheses are hybrids of natural and artificial components. For example, U.S. Pat. No. 4,546,500 to Bell discloses a method and apparatus for producing living blood vessels that incorporates a plastic mesh sleeve within the layers of the vessels. U.S. Pat. No. 3,626,947 to Sparks and U.S. Pat. No. 4,743,251 to Barra disclose methods for reinforcing veins and arteries with multiperforated flexible sheaths or textile mesh reinforcing tubes.

Other prostheses are wholly artificial. For example, U.S. Pat. No. 4,657,544 to Pinchuk describes a porous elastic cardiovascular graft without any wrap or exterior structure to provide strength or kink resistance. U.S. Pat. No. 2,990,605 to Demsyk describes an artificial vascular member that is formed from a Dacron tube but does not appear to be compliant. U.S. Pat. No. 4,610,688 to Silvestrini, et al. describes triaxiallybraided fabric vascular prostheses that may be made to be flexible in both longitudinal and radial directions, but does not have any exterior reinforcement for kink resistance or the like. U.S. Pat. No. 4,286,341 to Greer, et al. provides a vascular prosthesis with a woven or knitted support tube made from Dacron or other biocompatible fiber-forming materials. U.S. Pat. No. 4,550,447 to Seiler, Jr., et al. provides a vascular graft prosthesis with a porous tube reinforced by generally transverse external ribs. U.S. Pat. No. 3,479,670 to Medell discloses a tubular prosthetic implant composed of a knitted fabric tube wrapped with helical thermoplastic monofilament. U.S. Pat. No. 4,604,762 to Robinson discloses an arterial graft prosthesis that may be provided with a confining netting of Dacron or the like which loosely surrounds the remainder of the artificial artery in order to confine substantial expansions of the artificial artery.

As may be seen from the above survey, various approaches have been taken to provide completely or partially artificial vascular graft prostheses that have some, but not all, of the features of living blood vessels. Generally, a porous and flexible tube is provided to contain blood elements. A porous (necessary for ingrowth of surrounding tissue) wrap may be provided for radial and longitudinal strengthening and possibly for kink resistance. The tube may expand and contract in some of the prostheses, such as those of Pinchuk, Silvestrini, et al., and Robinson described above.

Currently available wraps on vascular prostheses provide radial and tensile strength and, in some cases, kink resistance. No wraps, apart from those of Robinson (U.S. Pat. No. 4,604,762), are known that also allow for compliance because existing wraps are in intimate contact with the walls of the vascular prostheses. Consequently, they restrict the expansion due to increasing blood pressure.

A need exists, therefore, for a vascular graft with a wrap which permits the graft to be compliant while providing radial and longitudinal strengthening and resistance to kinking.

SUMMARY OF THE INVENTION

Accordingly, an object of the present invention is to provide an improved vascular graft prosthesis.

The vascular graft prosthesis of the invention provides all the features required of a vascular graft prosthesis, including compliance. Compliance results from providing a space between the outer surface of an elastomeric tube and the inner surface of a flexible wrap. The space is controlled with ribs of flexible material. The space may be designed to accommodate the normal, physiological pulse pressure. Yet, when exorbitantly high pressures are encountered, the wrap provides radial strain protection.

The vascular graft prosthesis according to the invention provides for compliance, yet offers longitudinal and radial strength. In addition, it provides kink resistance. The pores of the wrap may be made large enough to provide ingrowth of tissues from the periadvential capsule and to allow needle puncture during renal dialysis.

The invention will appear more clearly from the following detailed description which, when read in connection with the accompanying drawings, will describe and show a preferred embodiment of the vascular graft prostheses according to the invention and a preferred method of making the same.

DETAIL DESCRIPTION OF THE PREFERRED EMBODIMENT

Figure 1:
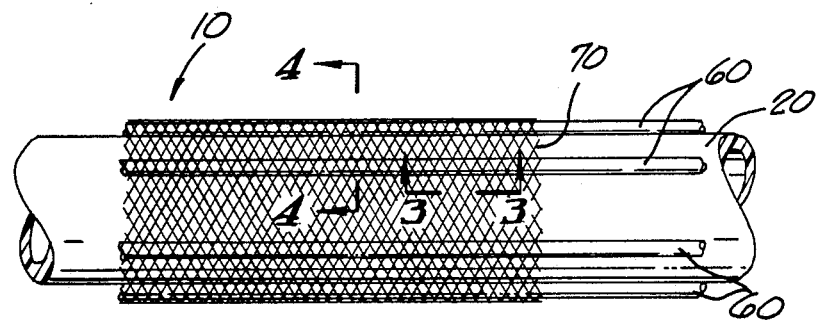
FIG. 1 is a side elevational view of the preferred embodiment of the vascular graft prosthesis according to the invention with part of the wrap removed.
Figure 2:
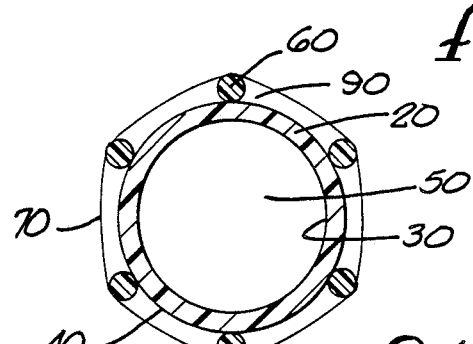
FIG. 2 is an end view of the prosthesis illustrated in FIG. 1.

Referring now to FIG. 1 in the drawings, the preferred embodiment of the vascular graft prosthesis 10 according to the invention is indicated generally by reference numeral 10. The prosthesis 10 is essentially cylindrical as a reference to the end view in FIG. 2 will confirm. A tube 20 is composed of a radially uniform and seamless wall which surrounds lumen 50. Tube 20 is made of an elastomeric biocompatible material and is designed to retain the blood elements. The material for tube 20 is preferably silicone rubber (such as Dow Corning's Q-7-4840) although other elastomeric biocompatible materials, such as polyurethane, may be used. The silicone rubber of the tube 20 has porosity (described below) which makes it elastomeric as well as flexible.

Vascular graft prostheses have been made according to the preferred embodiment of the invention and have been successful when implanted in dogs. The tube of one of these prostheses had an internal diameter (diameter of the lumen) of 4 mm, a 0.75 mm wall thickness, and an outer diameter of 5.5 mm. Another had a 6 mm internal diameter, 1.0 mm wall thickness, and 8 mm outer diameter.

Tube 20 is formed by the replamineform process described in U.S. Pat. No. 3,890,107 to White, et al. U.S. Pat. No. 3,890,107 to White, et al. is hereby incorporated by reference as if fully set forth herein. To briefly describe the replamineform process as applied in the preferred method of making the vascular graft prosthesis of the invention, tube 20 is formed by casting silicone rubber into a tube which serves as an investment. The tube is machined from the calcium carbonate skeleton of a marine invertebrate. The calcium carbonate skeleton of the spine of the sea urchin *Heterocentrotus mammillatus* is preferred for this method, although the coral Porites is acceptable. (The choice of marine invertebrate is based in part on the consistency and size of the porosity available.)

The calcium carbonate investment is later dissolved away, leaving a tube of porous silicone rubber. The wall of the tube, accordingly, has a three dimensional interconnected porosity. Porosity, at least at the inner peripheral surface 30 of tube 20, is recommended in order to permit ingrowth of a neointima, which will line the inner peripheral surface 30 of the tube 20. An average pore diameter in the range of 20 to 30 microns at the inner peripheral surface is preferred in order to encourage the growth of this lining. Formation of the tube 20 by the replamineform process provides three dimensional interconnected porosity throughout the wall of the tube 20; porosity therefore will be present at the inner peripheral surface 30 as well as at the outer peripheral surface 40.

The outer peripheral surface 40 of tube 20 has structure attached which provides radial and longitudinal strengthening to the prosthesis as well as kink resistance. Ribs 60 are attached to the outer peripheral surface 40 of the tube 20. Ribs 60 extend radially outward (best seen in FIG. 2) from the outer peripheral surface 40 of the tube and are aligned substantially parallel (best seen in FIG. 1) to the longitudinal axis of the tube. The ribs are spaced from each other and do not contact each other. Six ribs are provided in the preferred embodiment. The ribs are surrounded by a wrap or sleeve 70. The number and size of the ribs must be chosen so that the wrap 70 does not contact the outer peripheral surface 40 of the tube 20. The preferred rib diameter is in the range 500 microns to 1000 microns.

Figure 5:
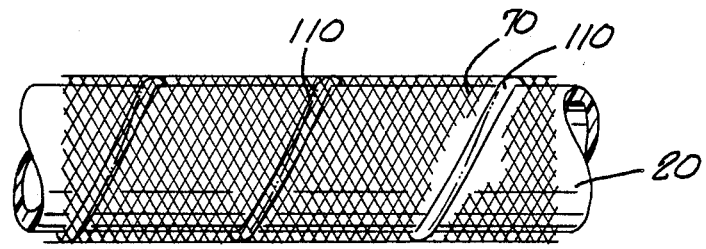
FIG. 5 is a side elevational view of an alternative embodiment of the vascular graft prosthesis according to the invention.
Figure 6:
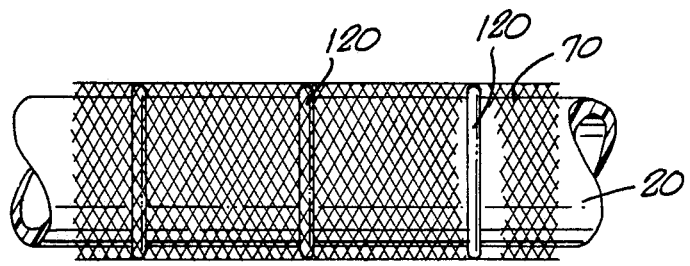
FIG. 6 is a side elevational view of a second alternative embodiment of the prosthesis.
Figure 7:
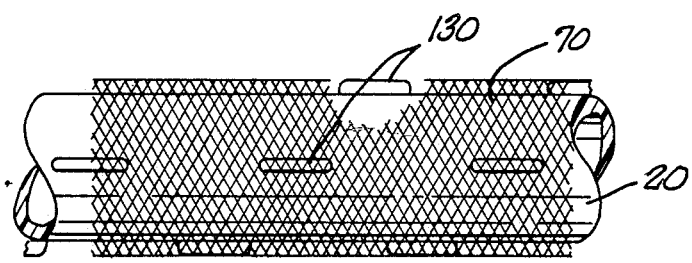
FIG. 7 is a side elevational view of a third alternative embodiment of the prosthesis.

The arrangement of the ribs may be varied from that of the preferred embodiment (radially outwardly spaced and longitudinally aligned) yet remain in accordance with the invention. FIGS. 5–7 depict some alternative embodiments of the invention showing helical ribs 110 (FIG. 5), ring-like ribs 120 (FIG. 6), and intermittent segment ribs 130 (FIG. 7). All provide space between the wrap and the tube as in the preferred embodiment.

Preferably, the ribs are made of solid silicone rubber (such as Dow Corning's Q-7-4840). Solid silicone rubber is flexible rather than elastomeric. Other flexible biocompatible materials may be used for the ribs, such as polyester, polypropylene, polyurethane, and polyethylene. Ribs 60 are injection molded at the outer peripheral surface and adhere to that surface upon hardening.

The wrap or sleeve 70 is flexible and must be perforated in order to provide for ingrowth of tissues from the periadvential capsule and for needle puncture (as in renal dialysis). The average pore diameter is recommended to be at least 100 microns and an average pore diameter in the range 500 microns to 750 microns is preferred. In the preferred embodiment, the sleeve or wrap is a weave of polyester strands or monofilaments, such as those provided by Bentley Harris. A woven sleeve of polytetrafluoroethylene (PTFE), also available from Bentley Harris, has been used and has been found to be acceptable. The weave or knit of the sleeve should be loose enough that the sleeve is perforated, as shown in FIG. 1. Other materials may be used that are flexible and biocompatible and can be woven or knitted so as to form an perforate sleeve or wrap, such as polypropylene and polyethylene.

The sleeve or wrap 70 is loosely stretched or placed over the entire prosthesis so that the wrap bridges between adjacent ribs 60, defining spaces 90 between the wrap, ribs, and outer peripheral surface 40 of the tube. Individual monofilaments 80 of the wrap (see FIG. 3) are held in place by applying a bead of liquid injection molded silicone rubber (such as Dow Corning's MDX-4-4210) at the ribs 60; the silicone rubber bonds the wrap to the ribs.

Figure 3:
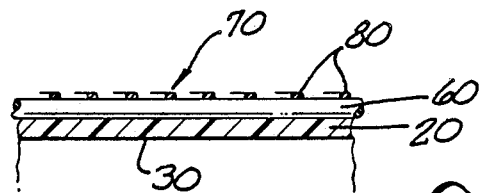
FIG. 3 is an enlarged sectional view taken along the line 3—3 of FIG. 1.

The enlarged sectional view seen in FIG. 3 depicts the structure of the tube, rib, and wrap complex. The ribs and the wrap together provide kink resistance as well as longitudinal strengthening. The wrap provides radial strain protection as described below.

Figure 4:
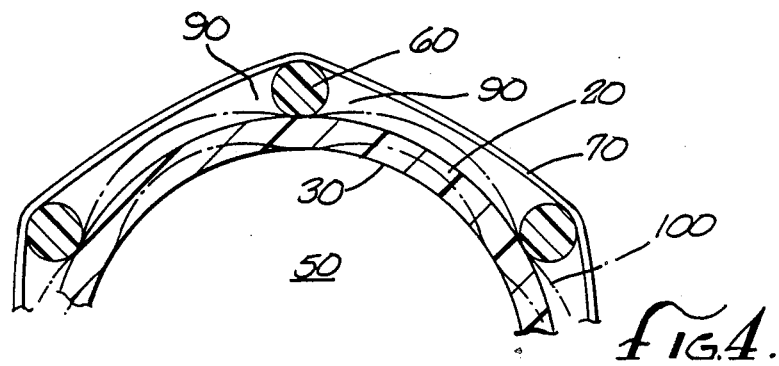
FIG. 4 is an enlarged sectional view taken along the line 4—4 of FIG. 1 with the expansion of the tube shown in phantom.

The silicone rubber of the tube is elastomeric and the tube 20 will tend to expand when pressure inside the lumen 50 increases due to the heart beat. The expansion of the tube 20 is controlled by the ribs 60 and the wrap 70. As seen in FIG. 4, the tube expands into spaces 90 which normally exist between the wrap and the outer peripheral surface 40 of the tube, even though collagen and loose connective tissue, which are elastomeric, will eventually fill these spaces. The expansion of the tube wall due to increased pressure in lumen 50 is shown in phantom lines indicated by reference numeral 100.

The radial expansion of the tube, however, is controlled by the provision of wrap 70. Depending on the size of the prosthesis, the size and spacing of ribs 60 must be chosen in conjunction with the thickness of the wall of tube 20 to provide a sufficiently large space 90 to permit expansion of tube 20 so that the prosthesis is substantially isocompliant with the artery or other blood vessel at the anastomosis. The result is an isocompliant prosthesis that has longitudinal and radial strength as well as kink resistance.

While a preferred embodiment of the invention and a method of making the same has been described, those skilled in the art will understand that changes and modifications may be made without departing from the spirit of the invention. Such equivalents to the specific prosthesis and method disclosed here, as may be ascertained by using no more than routine experimentation, are intended to be included within the scope of the appended claims.

What is claimed is:

1. A vascular graft prosthesis, comprising:
   a tube made of elastomeric biocompatible material, the tube having an outer peripheral surface and an inner peripheral surface, the inner peripheral surface defining a lumen;
   outwardly extending and spaced ribs made of a flexible biocompatible material and attached to the outer peripheral surface of the tube; and
   a perforate wrap of flexible biocompatible material circumferentially disposed about an attached to the ribs and radially spaced apart from the tube by the ribs, the wrap bridging between adjacent ribs and defining spaces between the outer peripheral surface of the tube and the wrap, thereby allowing the tube to expand and contract in response to changes in pressure in the lumen.

2. The vascular graft prosthesis according to claim 1 in which the vascular graft prosthesis is substantially isocompliant with a blood vessel having a lumen of equivalent diameter.

3. The vascular graft prosthesis according to claim 1 in which the ribs are radially spaced and are aligned on the outer peripheral surface of the tube substantially parallel to a longitudinal axis of the tube.

4. The vascular graft prosthesis according to claim 1 in which at least one rib is helically disposed at the outer peripheral surface of the tube.

5. The vascular graft prosthesis according to claim 1 in which the ribs are spaced intermittent segments disposed at the outer peripheral surface of the tube.

6. A vascular graft prosthesis, comprising:
   a tube made of elastomeric biocompatible material, the tube having an outer peripheral surface and an inner peripheral surface, the inner peripheral surface defining a lumen;
   a radial outwardly extending and spaced ribs made of a flexible biocompatible material attached to the outer peripheral surface of the tube and aligned thereon substantially parallel to a longitudinal axis of the tube; and
   a perforate sleeve comprising woven strands of flexible biocompatible material circumferentially disposed about and attached to the ribs and radially spaced apart from the tube, the sleeve bridging between adjacent ribs and defining spaces between the outer peripheral surface of the tube and the wrap, to allow the tube to expand and contract in response to changes in pressure in the lumen.

7. A method of making a vascular graft prosthesis, comprising the steps of:
   forming a tube from an elastomeric biocompatible material, the tube defining a lumen;
   attaching spaced ribs of a flexible biocompatible material at an outer peripheral surface of the tube so that the ribs extend outwardly therefrom; and
   attaching a perforate wrap of flexible biocompatible material over the ribs and spaced apart from the tube so that the wrap bridges between adjacent ribs to define spaces between the outer peripheral surface of the tube and the wrap, to allow the tube to expand and contract in response to changes in pressure in the lumen.

8. The prosthesis of claim 1 wherein at least the inner peripheral surface of the tube is porous.

9. The prosthesis of claim 1 wherein the tube is made by the replamineform process.

10. The prosthesis of claim 1 comprising 6 equally spaced ribs.

11. The prosthesis of claim 1 comprising ribs having diameters of from approximately 500 to 1000 microns.

12. The prosthesis of claim 1 comprising ribs of a material selected from the group consisting of solid silicone rubber, polyester, polypropylene, polyurethane, polyethylene and a combination thereof.

13. The prosthesis of claim 1 comprising a perforate wrap having an average pore diameter in the range of approximately 500 to 750 microns.

14. The prosthesis of claim 1 comprising a wrap of a material selected from the group consisting of polyester, polytetrafluoroethylene, polypropylene, polyethylene and a combination thereof.

15. The method of claim 7 further comprising the step of injection molding the ribs onto the outer peripheral surface of the tube.

16. The method of claim 7 further comprising the step of bonding individual monofilaments of the wrap to the ribs with beads of liquid injection molded silicone rubber.

* * * * *